(12) United States Patent
Schindler et al.

(10) Patent No.: US 8,899,827 B2
(45) Date of Patent: Dec. 2, 2014

(54) THERMAL ANALYSIS APPARATUS AND THERMAL ANALYSIS METHOD

(75) Inventors: Alexander Schindler, Leupoldsgruen (DE); Juergen Blumm, Selb (DE)

(73) Assignee: Netzsch-Gerätebau GmbH (DE)

( * ) Notice: Subject to any disclaimer, the term of this patent is extended or adjusted under 35 U.S.C. 154(b) by 269 days.

(21) Appl. No.: 13/311,329

(22) Filed: Dec. 5, 2011

(65) Prior Publication Data
US 2012/0096936 A1 Apr. 26, 2012

Related U.S. Application Data

(63) Continuation of application No. PCT/DE2010/000623, filed on Jun. 2, 2010.

(30) Foreign Application Priority Data

Jun. 5, 2009 (DE) .......................... 10 2009 024 055

(51) Int. Cl.
| | | |
|---|---|---|
| G01K 1/00 | (2006.01) | |
| G01K 17/00 | (2006.01) | |
| G01N 25/00 | (2006.01) | |
| G01N 17/00 | (2006.01) | |
| C01B 13/02 | (2006.01) | |

(52) U.S. Cl.
CPC .............. G01N 25/00 (2013.01); G01N 17/002 (2013.01); C01B 2210/0046 (2013.01); C01B 2210/0082 (2013.01); C01B 13/0281 (2013.01); C01B 2210/0079 (2013.01); C01B 13/0277 (2013.01)
USPC ........................................... 374/31; 374/141

(58) Field of Classification Search
USPC .................................................. 374/31, 141
See application file for complete search history.

(56) References Cited

U.S. PATENT DOCUMENTS

| | | | |
|---|---|---|---|
| 5,061,914 A | 10/1991 | Busch et al. | |
| 5,536,302 A | 7/1996 | Golden et al. | |
| 6,442,304 B1 * | 8/2002 | Crawley et al. | ................. 385/12 |
| 2010/0150204 A1 * | 6/2010 | Yamaguchi et al. | .......... 374/100 |

FOREIGN PATENT DOCUMENTS

| | | |
|---|---|---|
| DE | 2340102 A1 | 2/1974 |
| DE | 3621014 A1 | 1/1987 |
| DE | 68910638 T2 | 2/1994 |
| DE | 69830247 T2 | 5/2006 |

OTHER PUBLICATIONS

"Pressureless Infiltration of Al-Mg Based Alloys Into Al2O3 Preforms: Mechanisms and Phenomenology" by Rao et al (2001).*
"Thin Tantalum—Silicon—Oxygen/Tantalum—Silicon—Nitrogen films as High-Efficiency Humidity Diffusion Barriers for Solar Cell Encapsulation" by Hauer et al (2006).*
International Search Report; Application No. PCT/DE2010/000623; Issued: Aug. 30, 2010; Mailing Date: Sep. 13, 2010; 3 pages.
Rao, et al.; "Pressureless Infiltration of Al-Mg Based Alloys into Al2O3 Preforms: Mechanisms and Phenomenology"; Acta Materialia vol. 49; Issue 13, Aug. 2001; pp. 2373-2385 (2 page abstract only).
Heuer, et al.; "Thin tantalum—Silicon—Oxygen/Tantalum—Silicon—Nitrogen films as High-Efficiency Humidity Diffusion Barriers for Solar Cell Encapsulation"; Thin Solid Films; vol. 515, Issue 4, Dec. 2006; pp. 1612-1617 (2 page abstract only).

* cited by examiner

*Primary Examiner* — Mirellys Jagan
(74) *Attorney, Agent, or Firm* — St. Onge Steward Johnston & Reens LLC

(57) ABSTRACT

A thermal analysis apparatus and method, including a sample space with a sample carrier, and heating devices, and an inert gas. Flow devices generate an inert gas flow to the sample carrier. Getter devices and/or oxygen traps disposed in the inert gas flow remove residual oxygen.

22 Claims, 3 Drawing Sheets

THERMAL ANALYSIS APPARATUS AND THERMAL ANALYSIS METHOD

CROSS-REFERENCE TO RELATED APPLICATIONS

The present application is a continuation of pending International patent application PCT/DE2010/000623 filed on Jun. 2, 2010 which designates the United States and claims priority from German patent application 10 2009 024 055.1 filed on Jun. 5, 2009, the content of which is incorporated herein by reference.

FIELD OF THE INVENTION

The invention relates to a thermal analysis apparatus with a sample space, in which a sample carrier and heating devices as well as flow devices with an inert gas supply for an inert gas are contained. The invention also relates to a thermal analysis method wherein a sample carrier and heating devices are surrounded by inert gas in a sample space, and wherein an inert gas flow is generated by an inert gas supply in the sample space.

BACKGROUND OF THE INVENTION

Investigatory methods for material characterisation are referred to as thermal analysis, wherein the sample is subjected to a controlled temperature program. Dimensional changes, mass changes, calorific effects, the specific thermal capacity and escaping gases, for example, are investigated.

The samples may oxidise due to residual oxygen in an otherwise inert gas atmosphere provided in the sample space, which can falsify the results and is therefore undesirable. The presence of residual oxygen in the inert gas, which is also referred to and/or used as purging gas, in apparatus for measurements under a nominal inert gas atmosphere (e.g. nitrogen, argon or helium) therefore represents a problem.

Residual oxygen in an apparatus is usually minimised by the fact that the typically vacuum-tight apparatus is evacuated and then filled and purged with inert gas of high purity. The residual oxygen concentration thus depends on the vacuum tightness of the apparatus, the vacuum tightness of the gas supply lines and the purity of the inert gas present. Purification of the purging gas before entry into the apparatus is just inadequate due to the finite leakage rate of the apparatus itself and the desorption of residual oxygen from the walls of the apparatus.

Accordingly, although devices and methods for removing residual oxygen from an inert gas according to publications DE 2 340 102 A, DE 698 30 247 T2, DE 36 21 014 C2 and DE 689 10 638 T2 are suitable in principle for reducing the residual oxygen content of an inert gas, the purity of the inert gas in respect of residual oxygen in each case deteriorates again before the use of the inert gas due to its subsequent path into respective apparatuses. In certain production processes and production environments, such as are used for example as applications for inert gas in the aforementioned publications, this may possibly be acceptable, but satisfactory results are not thereby obtained for measurement and analysis apparatuses and methods, such as in particular thermal analysis apparatuses and methods.

SUMMARY OF THE INVENTION

It is therefore the aim of the invention to reduce and therefore improve the residual oxygen load in measurements with thermal analysis apparatuses and methods.

This aim is achieved with a thermal analysis apparatus as well as with the thermal analysis method.

The invention thus creates a thermal analysis apparatus with a sample space, in which a sample carrier and heating devices as well as an inert gas are contained, wherein furthermore flow devices for the inert gas for generating an inert gas flow to the sample carrier and getter devices (oxygen trap devices) for removing residual oxygen from the inert gas are contained, said getter devices being disposed in the inert gas flow in the flow direction upstream of the sample carrier in the vicinity thereof.

A considerable in situ reduction in the residual oxygen concentration in the thermal analysis apparatus at the site of the sample is achieved by the getter devices in an advantageous and inventive way.

Provision is also preferably made such that the getter devices are disposed in the inert gas flow in the flow direction upstream of the sample carrier at a distance therefrom.

It is also preferable for the flow devices for the inert gas to comprise an inert gas supply to the sample space.

A further advantageous embodiment consists in the fact that the getter devices comprise a getter carrier and an especially metallic getter material disposed therein or thereon, wherein provision can in particular also be made such that the getter carrier and/or the getter material are/is disposed in the flow direction of the inert gas upstream of the sample carrier and at least approximately axially aligned with the latter. Alternatively or additionally, provision can preferably be made such that the getter material is temperature-resistant,
the getter material contains zirconium,
the heating devices are designed, in particular constituted, shaped and/or disposed, so as to heat the getter material to a temperature of 400° C. or over,
the getter carrier is made at least essentially from a ceramic material, the ceramic containing in particular $Y_2O_3$,
the getter carrier is made at least essentially from a material which does not react with the getter material, and/or
the getter carrier is a rod, a wire or a ring.

A further preferred embodiment consists in the fact that the heating devices define a heating zone, in which the sample carrier together with a sample placed optionally thereon or therein and at least in part the getter devices, if appropriate at least the getter material, are disposed.

Provision can also preferably be made such that the heating devices are designed and disposed in such a way that they simultaneously heat a sample that can be placed on the sample carrier and at least in part the getter devices, if appropriate at least the getter material.

According to another preferred embodiment, provision is made such that the heating devices for heating a sample that can be placed on the sample carrier comprise at least one heating element which, with respect to the sample on or in the sample carrier, is laterally spaced apart from the latter, wherein provision can in particular also be made such that the heating element or the heating elements surrounds or surround the sample carrier laterally at least in part.

The flow devices are preferably designed and disposed so as to generate an at least essentially vertical inert gas flow, and the sample carrier is disposed at least essentially above the getter devices, so that the inert gas flow flows laterally past the sample carrier and past a sample that can be placed on the sample carrier. Alternatively, provision can also be made such that the flow devices are designed and disposed so as to generate an at least essentially horizontal inert gas flow, and that the sample carrier is disposed at least essentially laterally with respect to the getter devices, so that the inert gas flow flows at least over the sample carrier and a sample that can be placed on the sample carrier.

The inert gas preferably contains argon, in particular of purity 99.996, nitrogen and/or helium.

Furthermore, provision can preferably be made such that the sample carrier is designed to carry a crucible for receiving a sample to be investigated.

The oxygen trap devices preferably comprise getter devices.

The previously described embodiments especially of the getter devices, but also of the thermal analysis apparatus in general, are to be regarded as preferable.

Finally, the invention also creates a thermal analysis method, wherein a sample carrier and heating devices are surrounded by inert gas in a sample space, and wherein the inert gas is caused to flow as an inert gas flow in the sample space first over or past getter devices for the removal of residual oxygen from the inert gas and then to the sample carrier, which is disposed in the vicinity of the getter devices.

A preferred development thereof consists in the fact that the inert gas flow is generated with an inert gas supply to the sample space.

Provision can preferably also be made such that the heating devices define a heating zone, in which the sample carrier together with a sample placed optionally thereon or therein and at least in part the getter devices, if appropriate at least the getter material, are disposed, so that the heating devices simultaneously heat a sample that can be placed on the sample carrier and at least in part the getter devices or a getter material contained in the latter.

Another preferred embodiment of the thermal analysis method consists in the fact that an at least essentially vertical inert gas flow is generated which flows past the getter devices and then flows to the sample carrier disposed at least essentially above the latter, so that the inert gas flow flows laterally past the sample carrier and past a sample that can be placed on the sample carrier. Alternatively, provision can be made such that an at least essentially horizontal inert gas flow is generated which first flows past the getter devices and then flows to the sample carrier disposed at least essentially laterally with respect thereto, so that the inert gas flow flows at least partially over the sample carrier and a sample that can be placed on the sample carrier.

Furthermore, provision can be made such that the thermal analysis apparatus comprises a plurality of heating devices, with which the getter device and the sample can be heated independently of one another.

In an additional embodiment, the thermal analysis apparatus is operated without the latter previously being evacuated. With this embodiment, the sample space is solely exposed to an inert gas flow which washes over the getter device and subsequently the sample.

Further preferred and/or advantageous embodiments of the invention emerge from the claims and their combinations as well as all the present application documents.

BRIEF DESCRIPTION OF THE DRAWINGS

The invention is explained in greater detail below, solely by way of example, with the aid of examples of embodiment making reference to the drawing, in which.

DETAILED DESCRIPTION OF THE INVENTION

Figure 1:
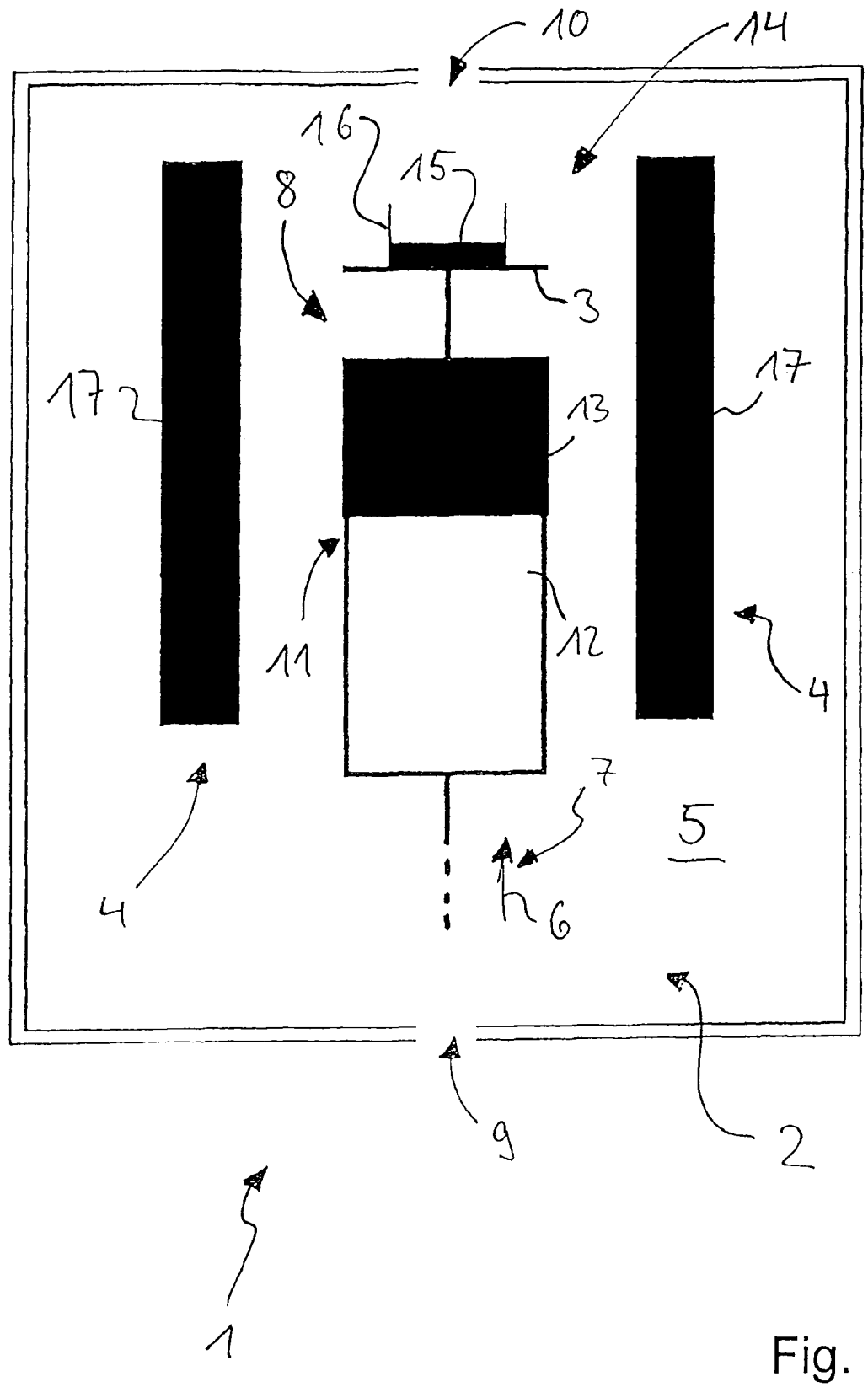
FIG. 1 shows in a diagrammatic representation a first example of embodiment of a thermal analysis apparatus.

Identical reference numbers in the individual figures and illustrations of the drawing denote identical or similar components or components acting identically or similarly. With the aid of the representations in the drawing, those features also become clear that are not provided with reference numbers, irrespective of whether such features are described below or not. On the other hand, features which are included in the present description, but are not visible or represented in the drawing, are readily understandable to the person skilled in the art.

Figure 2:
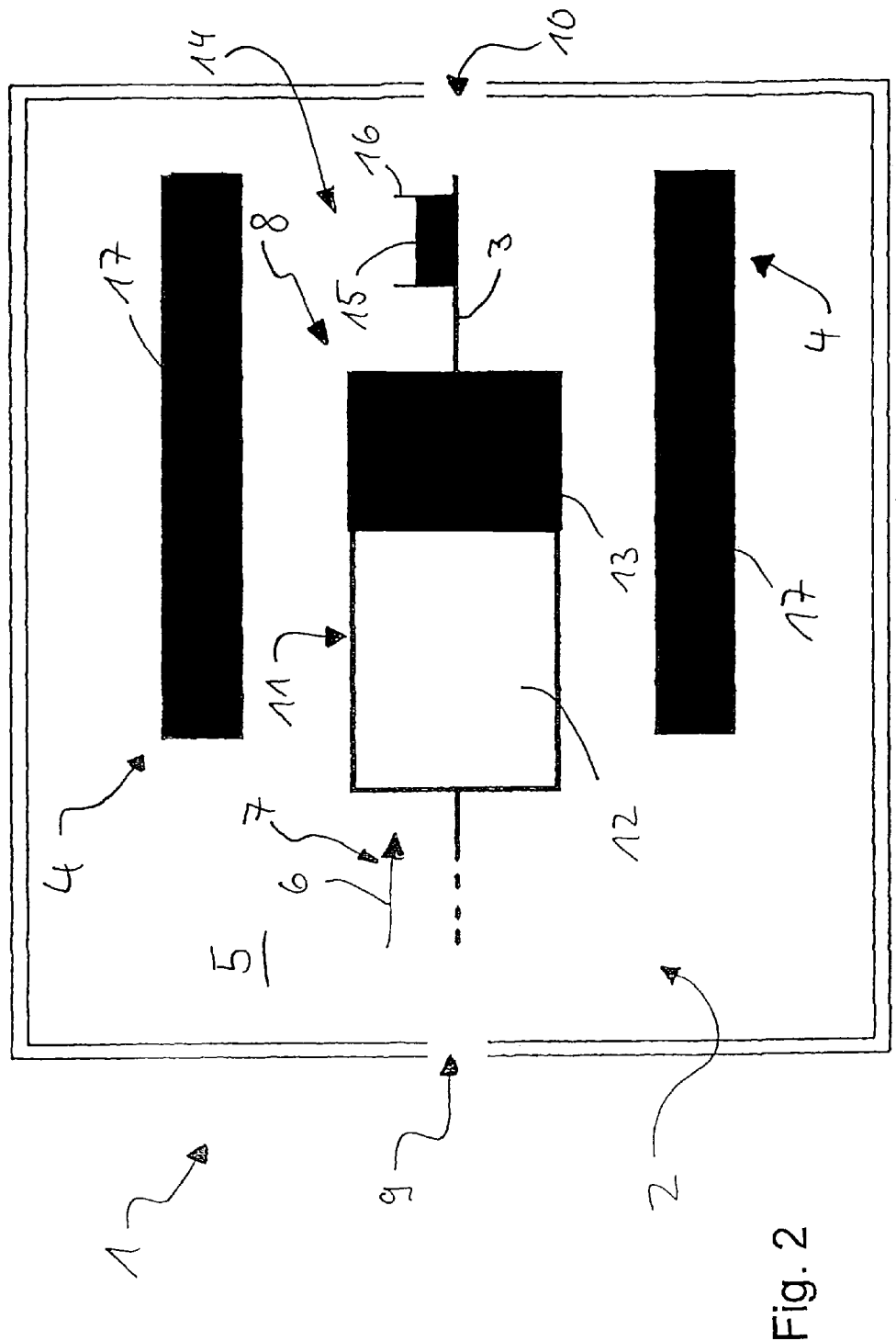
FIG. 2 shows in a diagrammatic representation a second example of embodiment of a thermal analysis apparatus.

A first and a second example of embodiment of a thermal analysis apparatus 1 are shown diagrammatically in FIGS. 1 and 2.

This thermal analysis apparatus 1 comprises a sample space 2, in which a sample carrier 3 and heating devices 4 as well as an inert gas 5 are contained. Flow devices 6 for inert gas 5 for generating an inert gas flow 7 to sample carrier 3 and oxygen trap devices 8 for the removal of residual oxygen from inert gas 5 are also contained. Flow devices 6 comprise an inert gas supply 9 to sample space 2, which further comprises an inert gas outlet 10, so that inert gas 5 flows from inert gas supply 9 to inert gas outlet 10 through sample space 2 and therein, in turn, from oxygen trap devices 8 to sample carrier 3.

Inert gas 5 is for example argon, in particular of purity 99.996, although gases such as for example nitrogen or helium or gas mixtures can also be used.

Oxygen trap devices 8 comprise getter devices 11 for the removal of residual oxygen from inert gas 5 and are disposed in inert gas flow 7 in the flow direction upstream of sample carrier 3 in the vicinity thereof, but spaced apart therefrom. The structure, function and action of getter devices are in principle known from the prior art, such as in particular from the publications mentioned at the outset, and a reference is expressly made here to the latter, so that all previously known embodiments of getter devices 11 and in particular the features disclosed in DE 2 340 102 A, DE 698 30 247 T2, DE 36 21 014 C2 and DE 689 10 638 T2 are included in their entirety by this mere reference in the present documents which is intended to avoid repetition.

Getter devices 11 comprise a getter carrier 12 and a getter material 13 disposed therein or thereon, said getter material containing in particular metals. Getter carrier 12 and/or preferably metallic getter material 13 are/is disposed in the flow direction of inert gas 5 or inert gas flow 7 upstream of sample carrier 3 and aligned approximately axially therewith. Heating devices 4 are designed, in particular constituted, shaped and/or disposed, so as to heat getter material 13 to a sufficiently high temperature (for example, above 400° C.). This temperature value, however, represents only an indication in the context of the example of embodiment; usable getter devices 11 and getter materials 13 are not restricted in the context of the present invention to those which work or act only from temperatures of 400° C. and over, but on the contrary use may also be made of getter devices 11 and getter materials 13 which work or act below 400° C. Getter material 13 is temperature-resistant and contains zirconium. Getter carrier 12 is made of a ceramic material, in particular $Y_2O_3$, and the material from which getter carrier 12 is made does not react with getter material 13. With regard to the embodiment, getter carrier 12 can be a rod, a wire or a ring.

Heating devices 4 define a heating zone 14, in which sample carrier 3 together with sample 15 in a crucible 16 placed thereon (see FIG. 1) or therein (see FIG. 2) and getter devices 11 or in general oxygen trap devices 8 are disposed. Getter devices 11 or oxygen trap devices 8 are therefore disposed in the flow direction of inert gas 5 or inert gas flow 7 upstream of sample carrier 3 spaced apart therefrom, in order to avoid reactions between sample 15 and getter material 13.

Furthermore, heating devices 4 are designed and disposed in such a way that they simultaneously heat sample 15 that can be placed on sample carrier 3 and getter devices 11 or at least their in particular metallic getter material 13. For this purpose, heating devices 4 comprise heating elements 17 which, with respect to sample 15 on or in sample carrier 3, are laterally spaced apart from the latter and which are formed and disposed in such a way that they surround sample carrier 3 laterally at least in part.

In the case of the first example of embodiment according to FIG. 1, thermal analysis apparatus 1 is disposed and embodied in such a way that flow devices 6 generate a vertical inert gas flow 7 from the bottom to the top as a result of the arrangement of inert gas supply 9 and inert gas outlet 10, sample carrier 3 then being disposed above getter devices 11, so that inert gas flow 7 flows laterally past sample carrier 3 and sample 15 placed on sample carrier 3.

As distinct therefrom, and this is the only distinction between the first and second example of embodiment, provision is made with thermal analysis apparatus 1 according to the second example of embodiment represented in FIG. 2 such that flow devices 6 are designed and disposed, through the arrangement of inert gas supply 9 and inert gas outlet 10, so as to generate a horizontal inert gas flow 7, and that sample carrier 3 is disposed laterally with respect to getter devices 11, so that inert gas flow 7 flows at least over the sample carrier and a sample that can be placed on the sample carrier.

According to the method, therefore, in sample space 2, which contains sample carrier 3 and heating devices 4 which are duly surrounded by inert gas 5, inert gas 5 is caused to flow, as inert gas flow 7 in sample space 2, first over or past getter devices 11 for the removal of residual oxygen from inert gas 5 and then to sample carrier 3, which is disposed spaced apart from getter devices 11, but in the vicinity thereof.

Of great importance in FIGS. 1 and 2 is the flow direction of the inert gas, i.e. inert gas flow 7, by means of which residual oxygen in inert gas 5 first passes to getter material 13 containing metals, is absorbed by the latter and thus does not pass to the site of sample 15. The selection of the vertical or horizontal arrangement can be made on the basis of further demands made on that the apparatus and/or the measurements.

Figure 3:
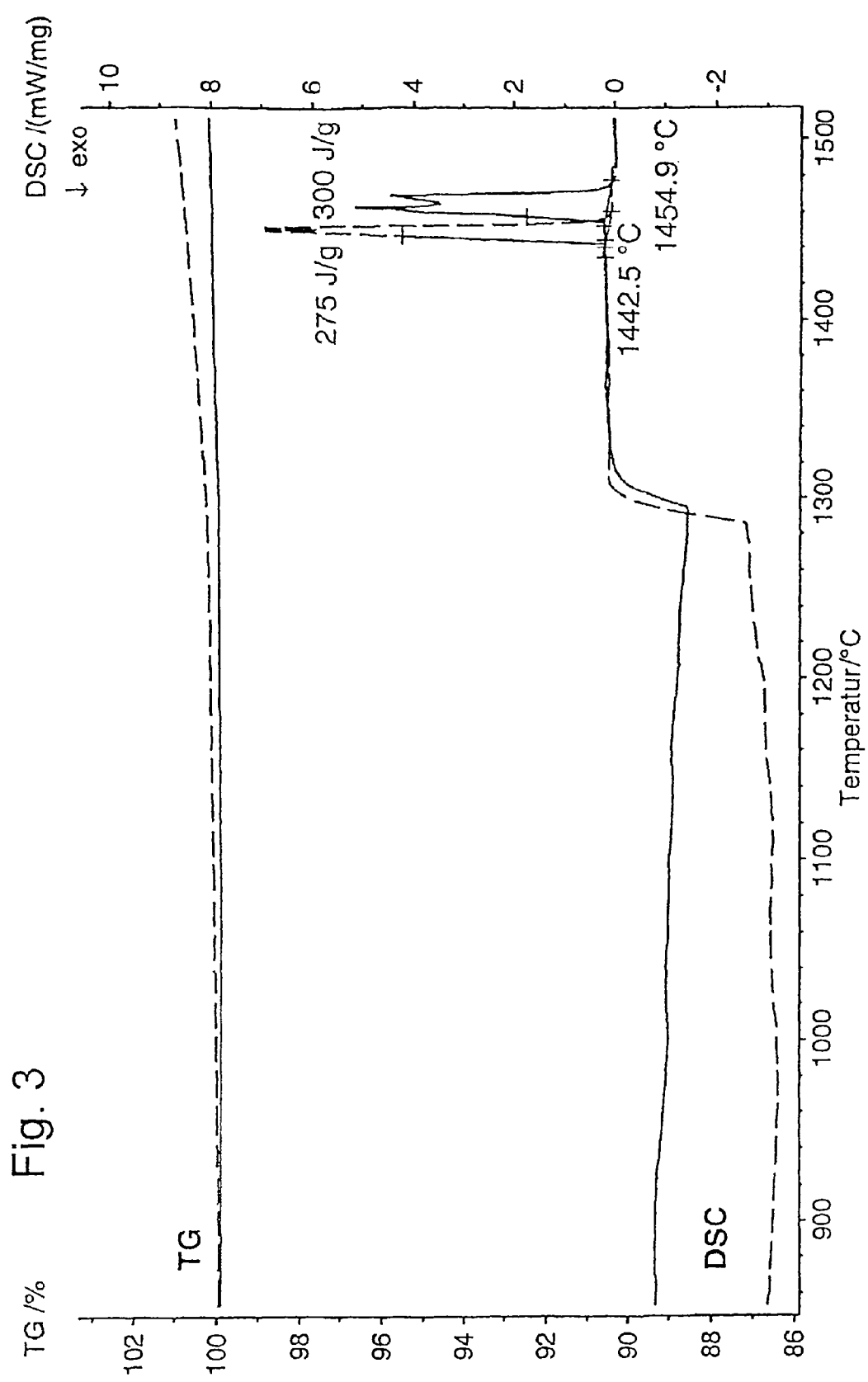
FIG. 3 shows measurement diagrams to illustrate the effect of the use of a thermal analysis apparatus according to the invention.

The mode of operation of thermal analysis apparatus 1 and of the thermal analysis method performed therewith and in particular of oxygen trap devices 8 or getter devices 11 disposed according to the invention in inert gas flow 7 upstream of sample 15 and its sample holder 3 becomes clear, by way of example, with the aid of the TG-DSC measurement curves shown in FIG. 3 and obtained with nickel. Two nickel samples were measured, and more precisely a nickel sample with thermal analysis apparatus 1 and the thermal analysis method performed therewith and in particular oxygen trap devices 8 or getter devices 11 disposed according to the invention in inert gas flow 7 upstream of sample 15 and its sample holder 3 with the result represented by the continuous line, and a nickel sample without oxygen trap devices 8 or getter devices 11 disposed in inert gas flow 7 upstream of sample 15 and its sample holder 3.

TG denotes thermal gravimetry, i.e. the determination of mass changes, and DSC denotes differential scanning calorimetry, wherein calorific effects, such as melting for example, can be investigated. Both measurements were carried out with argon purging gas of purity 99.996. The melting point ($T_{melt}$) of nickel of 1455° C. known from the literature is often used in thermal analysis apparatuses for thermometry at high temperatures. However, nickel is very oxidation-sensitive, as a result of which the melting point falls in an undefined manner and should therefore no longer be used for thermometry.

The measurement with thermal analysis apparatus 1 and the thermal analysis method performed therewith and in particular oxygen trap devices 8 or getter devices 11 disposed according to the invention in inert gas flow 7 upstream of sample 15 and its sample holder 3 delivers in this regard correct results, as the measurement curve represented with a continuous line shows: Sample 15 no longer oxidises significantly, which can be recognised by the horizontally running TG curve; no weight change occurs. The so-called DSC melting peak of nickel occurs at 1454.9° C., i.e. close to the literature value of 1455° C., the detected melting enthalpy delta H amounts to 299.8 J/g, i.e. approx. 300.0 J/g.

During the measurement without oxygen trap devices 8 or getter devices 11 disposed according to the invention in inert gas flow 7 upstream of sample 15 and its sample holder 3, sample 15 oxidises, which can be recognised by the markedly increasing TG curve according to the measurement curve represented by a dashed line (weight increase). The DSC melting peak already occurs at 1443° C. on account of the oxidation, i.e. 12° C. below the literature value. The measured melting enthalpy of 275 J/g also turns out to be less than the literature value of 300 J/g.

Thermal analysis apparatus 1 and the thermal analysis method performed therewith as well as in particular oxygen trap devices 8 or getter devices 11 disposed according to the invention in inert gas flow 7 upstream of sample 15 and its sample holder 3 enables an in situ reduction in the residual oxygen concentration in the thermal analysis measurements (TGA, DSC, STA, DIL etc.), and is constituted such that a particularly temperature-resistant getter material 13 is introduced into measuring or sample space 2 of thermal analysis apparatus 1. In the manner required at the given time, getter material 13 is brought by heating element 17 to a sufficiently high temperature in order to be able to work. The residual oxygen in inert gas 5 in sample space 2 is absorbed by getter material 13, and oxidation of sample 15 is thus effectively prevented. For this purpose, getter material 13 is positioned in thermal analysis apparatus in such a way that inert gas 5 first flows past getter material 13 and then past sample 15. Getter material 13 has no contact with crucible 16 and sample 15. Temperature-resistant getter carrier 12 positions getter material 13 accordingly in sample space 2 of thermal analysis apparatus 1. Getter carrier 12 comprises a material, such as for example a $Y_2O_3$ ceramic, which does not react with getter material 13.

In particular, all the individual features and possible embodiments of the invention and its examples of embodiment can be combined.

What is claimed is:

1. A thermal analysis apparatus comprising:
a sample space,
a sample carrier and heating devices contained within the sample space,
flow devices with an inert gas supply for an inert gas, the flow devices being contained within the sample space, and
at least one getter device for the removal of residual oxygen from the inert gas, the getter device being contained within the sample space,
wherein the at least one getter device is disposed in the inert gas flow in the flow direction upstream of the sample carrier and a distance apart from the sample carrier, and
the getter device includes at least one getter carrier for receiving a getter material, the getter carrier and/or the getter material being disposed axially with respect to the sample carrier, and the getter carrier being produced at least from a ceramic material.

2. The thermal analysis apparatus according to claim 1, characterized in that the getter carrier is made from a material which does not react with the getter material.

3. The thermal analysis apparatus according to claim 1, characterized in that the getter carrier is a rod, a wire or a ring.

4. The thermal analysis apparatus according to claim 1, characterized in that the heating devices are designed, constituted, formed and/or disposed in such a way that the getter material can be heated to a temperature of 400° C. or over.

5. The thermal analysis apparatus according to claim 1, characterized in that the heating devices are designed and disposed in such a way that a sample present on the sample carrier and at least in part the getter device can be heated simultaneously with the heating devices.

6. The thermal analysis apparatus according to claim 1, characterized in that the getter device comprises a separate heating device, with which the getter device can be heated separately and/or can be held at a specific temperature.

7. The thermal analysis apparatus according to claim 1, characterized in that the flow devices are designed such that an essentially vertical and/or horizontal inert gas flow is generated, and that the sample carrier is disposed above the getter devices and/or laterally with respect to the getter devices, so that the inert gas flow flows past laterally and/or above the sample carrier and a sample that can be placed on the sample carrier.

8. The thermal analysis apparatus according to claim 1, characterized in that the inert gas comprises argon and/or nitrogen and/or helium, in particular of purity 99.996.

9. The thermal analysis apparatus according to claim 1, characterized in that the sample carrier is designed to carry a crucible for receiving a sample to be investigated.

10. The thermal analysis apparatus according to claim 1, characterized in that the thermal analysis apparatus can be operated solely with the use of the inert gas flow without the thermal analysis apparatus previously having been provided with a vacuum.

11. The thermal analysis apparatus according to claim 1, characterized in that the getter material is a temperature-resistant metallic material and/or a material containing metals.

12. The thermal analysis apparatus according to claim 11, characterized in that the getter material is a material containing zirconium.

13. The thermal analysis apparatus according to claim 1, characterized in that the getter carrier is made at least partially from a ceramic material.

14. The thermal analysis apparatus according to claim 13, characterized in that the getter carrier is made at least partially from $Y_2O_3$.

15. The thermal analysis apparatus according to claim 1, characterized in that the heating devices define a heating zone, in which the sample carrier together with a sample placed thereon or therein and at least in part the getter device or at least the getter material are disposed.

16. The thermal analysis apparatus according to claim 15, characterized in that the heating devices for heating a sample present on the sample carrier are provided with at least one heating element laterally spaced apart from the sample.

17. The thermal analysis apparatus according to claim 15, characterized in that the heating element or the heating elements surrounds or surround the sample carrier laterally at least in part.

18. A thermal analysis method, wherein a sample carrier and heating devices are surrounded by inert gas in a sample space, wherein an inert gas flow is generated by an inert gas supply in the sample space, characterized in that
the inert gas flow in the sample space first flows over or past a getter device for the removal of residual oxygen from the inert gas and then to the sample carrier,
the getter device is disposed a distance a art from the sample carrier,
at least one getter carrier for receiving a getter material is disposed in the getter device, wherein the getter carrier and/or the getter material are aligned axially with the sample carrier, and
the getter carrier is produced from a ceramic material.

19. The thermal analysis method according to claim 18, characterized in that the heating devices define a heating zone, in which the sample carrier together with a sample placed thereon and/or therein and the getter device, and/or the getter material, are disposed in such a way that the sample placed on the sample carrier and/or the getter device and/or the getter material contained in the latter are heated by the heating devices.

20. The thermal analysis method according to claim 18, characterized in that a vertical and/or a horizontal inert gas flow is generated, which first flows past the getter device and then to the sample carrier disposed above and/or laterally with respect to the latter, so that the inert gas flow is conveyed laterally past and/or over the sample carrier and a sample placed on the sample carrier.

21. The thermal analysis method according to claim 18, characterized in that the heating devices are disposed in such a way that the getter device are heated by one heating device and the sample carrier with the sample is heated by another heating device.

22. The thermal analysis method according to claim 18, characterized in that the thermal analysis method is conducted by purging with the inert gas flow without the sample space previously having been evacuated.

* * * * *